US012211215B2

(12) United States Patent
Yoo et al.

(10) Patent No.: US 12,211,215 B2
(45) Date of Patent: Jan. 28, 2025

(54) APPARATUS AND METHOD FOR SUPPORTING ATTENTION TEST BASED ON ATTENTION MAP AND ATTENTION MOVEMENT MAP

(71) Applicant: Electronics and Telecommunications Research Institute, Daejeon (KR)

(72) Inventors: Jang-Hee Yoo, Daejeon (KR); Ho-Won Kim, Daejeon (KR); Jae-Yoon Jang, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 415 days.

(21) Appl. No.: 17/533,741

(22) Filed: Nov. 23, 2021

(65) Prior Publication Data
US 2022/0392080 A1    Dec. 8, 2022

(30) Foreign Application Priority Data

Jun. 3, 2021  (KR) .......... 10-2021-0072149
Jul. 26, 2021  (KR) .......... 10-2021-0097949

(51) Int. Cl.
| G06K 9/00 | (2022.01) |
| A61B 5/16 | (2006.01) |
| G06T 7/11 | (2017.01) |
| G06T 7/20 | (2017.01) |
| G06T 7/70 | (2017.01) |

(Continued)

(52) U.S. Cl.
CPC .............. *G06T 7/20* (2013.01); *A61B 5/163* (2017.08); *A61B 5/168* (2013.01); *G06T 7/11* (2017.01); *G06T 7/70* (2017.01); *G06V 20/40* (2022.01); *G06V 40/161* (2022.01); *G06T 2207/10016* (2013.01); *G06T 2207/30201* (2013.01)

(58) Field of Classification Search
CPC ....................................................... A61B 5/168
See application file for complete search history.

(56) References Cited

U.S. PATENT DOCUMENTS 7,120,880 B1 * 10/2006 Dryer ................. G06Q 30/02
                                              715/831
9,740,949 B1 *  8/2017 Khosla ................ G06V 10/451
(Continued)

FOREIGN PATENT DOCUMENTS

KR    1020120124772 A    11/2012
KR      101490040 B1      2/2015
(Continued)

*Primary Examiner* — Hadi Akhavannik
(74) *Attorney, Agent, or Firm* — William Park & Associates Ltd.

(57) ABSTRACT

Disclosed herein is a method for supporting an attention test based on an attention map and an attention movement map. The method includes generating a score distribution for each segment area of frames satisfying preset conditions, among frames of video content (video) that is produced in advance so as to be suitable for the purpose of a test, generating an attention map corresponding to the frames based on the distribution of the gaze point of a subject, generating an attention movement map corresponding to the frames based on information about movement of the gaze point of the subject, and calculating the attention of the subject using the score distribution for each segment area, the attention map, and the attention movement map.

20 Claims, 8 Drawing Sheets

(51) Int. Cl.
*G06V 20/40* (2022.01)
*G06V 40/16* (2022.01)

(56) References Cited

U.S. PATENT DOCUMENTS

| | | | |
|---|---|---|---|
| 10,593,118 B2* | 3/2020 | Bostick | G06F 8/30 |
| 10,867,211 B2* | 12/2020 | Thiebaut | G06V 20/46 |
| 11,645,930 B2* | 5/2023 | Trim | G09B 5/02 |
| | | | 434/310 |
| 2014/0086553 A1* | 3/2014 | Moon | H04N 21/44218 |
| | | | 386/239 |
| 2015/0339363 A1* | 11/2015 | Moldoveanu | G09B 19/00 |
| | | | 707/723 |
| 2016/0078614 A1* | 3/2016 | Ryu | G06T 7/12 |
| | | | 382/128 |
| 2016/0162745 A1* | 6/2016 | Cohen-Solal | G06F 3/013 |
| | | | 382/128 |
| 2018/0047164 A1* | 2/2018 | Ryu | G06T 7/12 |
| 2018/0075291 A1* | 3/2018 | Tian | G06V 40/172 |
| 2019/0340817 A1* | 11/2019 | Bostick | G06F 3/04815 |
| 2020/0074647 A1 | 3/2020 | Moon et al. | |
| 2020/0097076 A1* | 3/2020 | Alcaide | G06F 3/012 |
| 2020/0151875 A1* | 5/2020 | Song | G06V 10/82 |
| 2020/0292825 A1* | 9/2020 | Grundhoefer | G02B 27/0179 |

FOREIGN PATENT DOCUMENTS

| | | |
|---|---|---|
| KR | 1020150021810 A | 3/2015 |
| KR | 1020180021991 A | 3/2018 |
| KR | 1020190140767 A | 12/2019 |
| KR | 2020200000680 U | 3/2020 |

* cited by examiner

APPARATUS AND METHOD FOR SUPPORTING ATTENTION TEST BASED ON ATTENTION MAP AND ATTENTION MOVEMENT MAP

CROSS REFERENCE TO RELATED APPLICATION

This application claims the benefit of Korean Patent Application Nos. 10-2021-0097949, filed Jul. 26, 2021 and 10-2021-0072149, filed Jun. 3, 2021, which are hereby incorporated by reference in their entireties into this application.

BACKGROUND OF THE INVENTION

1. Technical Field

Generally, the present invention relates to technology for measuring the attention of a subject in an automatic manner by tracking the gaze point of the subject.

More particularly, the present invention relates to technology for generating a score distribution by segmenting an object of interest in video content into component units and for measuring the attention of a subject.

Also, the present invention relates to technology for measuring the attention of a subject using an attention map, which is generated based on information about the distribution and frequency of the gaze point of the subject, and an attention movement map, which is generated based on information about movement of the gaze point of the subject.

2. Description of the Related Art

In the mental health field, among medical fields, testing based on subject observation using checklists or questionnaires is used as an important screening or diagnosis method. Particularly, when mental health diagnosis, such as Autism Spectrum Disorder (ASD), Attention-Deficit Hyperactivity Disorder (ADHD), or the like, is made, it is essential to perform a test based on observation using checklists.

However, in the case of a test based on observation, some subjective factors of the tester, which are affected by the background, culture, experience, and the like of the tester, may be reflected in the test, whereby test results may vary. In some tests, perceptual characteristics, visual attention, and the like are analyzed using an eye tracker, and the result thereof is used for an ASD test, an infant development test, and the like, but eye trackers are very limitedly applicable.

Also, when an eye tracker is used for a test for infants/children, there are various issues affecting the method of using the eye tracker, such as calibration, which is essential for accurate eye-tracking and which requires prior consultation.

Also, in the case of ASD, cognitive characteristics, such as difficulty paying focused attention in response to a learning stimulus, a short attention span, difficulty transferring attention, and the like, may be observed. In the case of ADHD, characteristics in which it is difficult to maintain focused attention in an irritating situation or to pay attention to two or more things at the same time are commonly observed.

Accordingly, analysis of the attention of a subject may be used as an important measurement factor in a development test when an important assessment is made, but there is only a limited number of methods through which a tester can objectively and accurately measure the attention of a subject.

In conclusion, because determination in most attention tests for infants is based on a medical examination based on an interview or on an observation-based test due to the above-described problems, the tests may have a reliability issue.

Representative infant development tests capable of being performed in Korea include general development tests, such as Korean Developmental Screening Test for Infants and Children (K-DST), Korean Child Development Inventory (K-CDI), Developmental assessment for Early intervention Program planning (DEP), Ages and Stages Questionnaire (ASQ), Bayley Scales of Infant Development (Bayley), and the like, linguistic development tests, such as Preschool Receptive-Expressive Language Scale (PRES) and Sequenced Language Scale for Infants (SELSI), ASD and ADHD tests, such as Childhood Autism Rating Scale (CARS), The Autism Checklist (AUCL), Attention Deficit Hyperactivity Disorder Diagnostic Scale (ADHDDS), and Attention Deficit Hyperactivity Disorder-Symptom Checklist (ADHD-SC), and the like.

However, infant development tests are generally performed using checklists. That is, most tests are performed in such a way that parents, primary caregivers, or teachers of infants tick appropriate boxes on a check list after observing the infants or in such a way that the response of a subject observed during an interaction between a tester and the subject is checked according to the protocol presented in the check list.

Accordingly, it is necessary to perform an objective screening or diagnosis test by developing an automated apparatus and method capable of assisting such a test process.

Documents of Related Art (Patent Document 1) Korean Patent Application Publication No. 10-2012-0124772, titled "Apparatus and method for analyzing attention of a user"

(Patent Document 2) Korean Patent Application Publication No. 10-2019-0140767, titled "Apparatus and method for measuring degree of immersion"

(Patent Document 3) Korean Patent Application Publication No. 20-2020-0000680, titled "Device for improving study concentration".

SUMMARY OF THE INVENTION

An object of the present invention is to provide a method for segmenting objects of interest in video frames into component units and generating a score distribution for each segment area, thereby automatically calculating the attention of a subject.

Another object of the present invention is to provide a method for accurately and objectively measuring the attention of a subject using all of the frequency of the gaze point of the subject, the distribution thereof, and information about movement thereof.

In order to accomplish the above objects, a method for supporting an attention test based on an attention map and an attention movement map according to an embodiment of the present invention includes generating a score distribution for each segment area of frames satisfying preset conditions, among frames of video, generating an attention map corresponding to the frames based on a distribution of the gaze point of a subject, generating an attention movement map corresponding to the frames based on information about movement of the gaze point of the subject, and calculating the attention of the subject using the score distribution for each segment area, the attention map, and the attention movement map.

Here, generating the score distribution for each segment area may include detecting an object of interest in the frames, segmenting the object of interest into component units, and generating the score distribution for each segment area based on the result of segmentation of the object of interest into the component units.

Here, generating the score distribution for each segment area may comprise generating a score distribution for each segment area that represents frames in a preset time section in the video.

Here, generating the attention map and generating the attention movement map may comprise generating the attention map and the attention movement map that represent the frames in the preset time section.

Here, the score distribution for each segment area, the attention map, and the attention movement map may be generated in 2-dimensional pattern forms corresponding to a frame of the video.

Here, calculating the attention of the subject may comprise calculating the attention based on the result of operation performed on the values of the 2-dimensional pattern forms of the score distribution for each segment area, the attention map, and the attention movement map.

Here, calculating the attention of the subject may include supporting screening or diagnosis of the subject in an automatic manner based on the attention map, the attention movement map, and the result of analysis of the correlation between the result of calculating the attention and a development test result of the subject.

Here, the attention movement map may include information about whether the gaze point of the subject stays in a specific area for a time longer than a preset time and the information about the movement of the gaze point.

Here, the preset time may be set in advance based on movement and speed information of the object of interest.

Here, generating the attention map may include detecting a face area in an image of the subject, detecting the coordinates of the gaze point of the subject, and correcting the coordinates of the gaze point based on the head pose of the subject.

Here, the video corresponds to various video content produced in advance so as to be suitable for a test field and the purpose of a test.

Also, in order to accomplish the above objects, an apparatus for supporting an attention test based on an attention map and an attention movement map according to an embodiment of the present invention includes a video contents management unit for generating a score distribution for each segment area of frames satisfying preset conditions, among frames of video, an attention measurement unit for generating an attention map corresponding to the frames based on a distribution of the gaze point of a subject and generating an attention movement map corresponding to the frames based on information about movement of the gaze point of the subject, and an attention analysis unit for calculating the attention of the subject using the score distribution for each segment area, the attention map, and the attention movement map.

Here, the video contents management unit may detect an object of interest in the frames, segment the object of interest into component units, and define the score distribution for each segment area based on the result of segmentation of the object of interest into the component units.

Here, the video contents management unit may generate a score distribution for each segment area that represents frames in a preset time section in the video.

Here, the attention measurement unit may generate the attention map and the attention movement map that represent the frames in the preset time section.

Here, the score distribution for each segment area, the attention map, and the attention movement map may be generated in 2-dimensional pattern forms corresponding to a frame of the video.

Here, the attention analysis unit may calculate the attention based on the result of operation performed on the values of the 2-dimensional pattern forms of the score distribution for each segment area, the attention map, and the attention movement map.

Here, the attention analysis unit may support screening or diagnosis of the subject in an automatic manner based on the attention map, the attention movement map, and the result of analysis of the correlation between the result of calculating the attention and a development test result of the subject.

Here, the attention movement map may include information about whether the gaze point of the subject stays in a specific area for a time longer than a preset time and the information about the movement of the gaze point.

Here, the preset time may be set based on movement and speed information of the object of interest.

Here, the attention measurement unit may detect a face area in an image of the subject, detect the coordinates of the gaze point of the subject, and correct the coordinates of the gaze point based on the head pose of the subject, thereby generating the attention map and the attention movement map.

Here, the video may correspond to various video content produced in advance so as to be suitable for a test field and the purpose of a test.

BRIEF DESCRIPTION OF THE DRAWINGS

The above and other objects, features, and advantages of the present invention will be more clearly understood from the following detailed description taken in conjunction with the accompanying drawings, in which.

DESCRIPTION OF THE PREFERRED EMBODIMENTS

Figure 1:
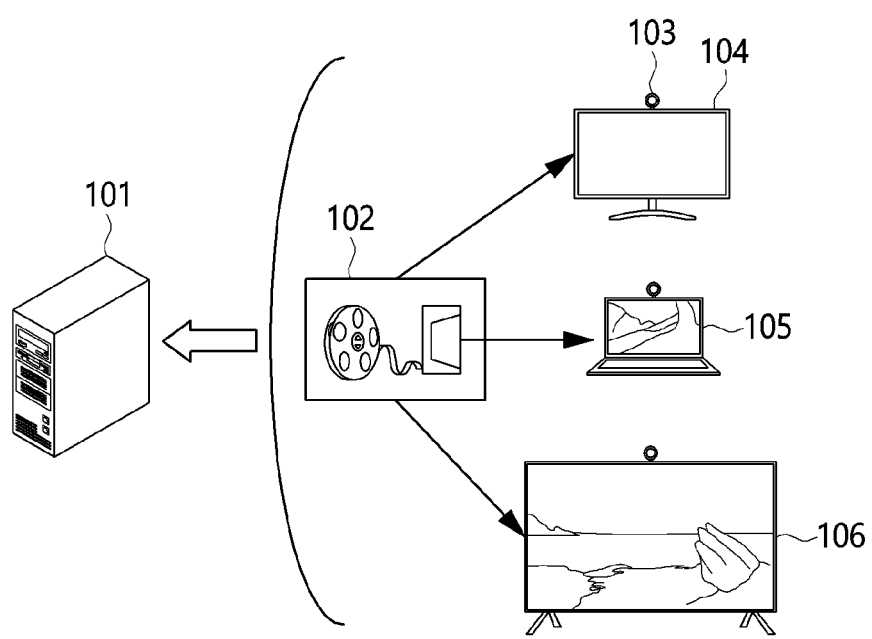
FIG. 1 is a conceptual diagram illustrating the configuration of an apparatus for supporting an attention test based on an attention map and an attention movement map according to an embodiment of the present invention.

The advantages and features of the present invention and methods of achieving the same will be apparent from the exemplary embodiments to be described below in more detail with reference to the accompanying drawings. However, it should be noted that the present invention is not limited to the following exemplary embodiments, and may be implemented in various forms. Accordingly, the exemplary embodiments are provided only to disclose the present invention and to let those skilled in the art know the category of the present invention, and the present invention is to be defined based only on the claims. The same reference numerals or the same reference designators denote the same elements throughout the specification.

It will be understood that, although the terms "first," "second," etc. may be used herein to describe various elements, these elements are not intended to be limited by these terms. These terms are only used to distinguish one element from another element. For example, a first element discussed below could be referred to as a second element without departing from the technical spirit of the present invention.

The terms used herein are for the purpose of describing particular embodiments only, and are not intended to limit the present invention. As used herein, the singular forms are intended to include the plural forms as well, unless the context clearly indicates otherwise. It will be further understood that the terms "comprises," "comprising,", "includes" and/or "including," when used herein, specify the presence of stated features, integers, steps, operations, elements, and/or components, but do not preclude the presence or addition of one or more other features, integers, steps, operations, elements, components, and/or groups thereof.

Unless differently defined, all terms used herein, including technical or scientific terms, have the same meanings as terms generally understood by those skilled in the art to which the present invention pertains. Terms identical to those defined in generally used dictionaries should be interpreted as having meanings identical to contextual meanings of the related art, and are not to be interpreted as having ideal or excessively formal meanings unless they are definitively defined in the present specification.

Hereinafter, embodiments of the present invention will be described in detail with reference to the accompanying drawings. In the following description of the present invention, the same reference numerals are used to designate the same or similar elements throughout the drawings, and repeated descriptions of the same components will be omitted.

FIG. 1 is a conceptual diagram illustrating the configuration of an apparatus for supporting an attention test based on an attention map and an attention movement map according to an embodiment of the present invention.

Referring to FIG. 1, the apparatus for supporting an attention test based on an attention map and an attention movement map according to an embodiment of the present invention includes previously produced video content 102. The video content 102 may be played and used in all smart devices in which a camera 103 is installed.

Here, a terminal for playing the video content 102 may be a display unit included in the apparatus for supporting an attention test, or may be a user terminal connected with the apparatus for supporting an attention test over a network.

Here, the user terminal may include a smart phone, a notebook computer, a personal computer (PC), a tablet personal computer (tablet PC), and a smart TV.

However, when video is played using a computer monitor 104, a notebook computer 105, a TV 106, or the like, which has a sufficiently large screen and is fixed to face forwards, it may be easy to track a gaze or a gaze point.

Here, the face area of a subject is captured using the camera 103 attached to a display device, and the head pose and the gaze point are analyzed, whereby an attention map and an attention movement map may be generated.

Also, the gaze of a subject may be tracked using an existing commercial eye tracker when calibration thereof is possible.

Here, the commercial eye tracker may be generally mounted onto the lower part of a monitor, and an attention map may be generated based on a tracking result acquired from the eye tracker.

Also, the previously produced content may be managed using a computer device 101, and the captured face image may also be analyzed in the computer device 101.

The computer device 101 may store and process information that is necessary for analysis of attention, such as main scene information, information about an object of interest and segmentation of the object of interest into components, a score distribution for each segment area, and the like, as well as the previously produced content.

Figure 2:
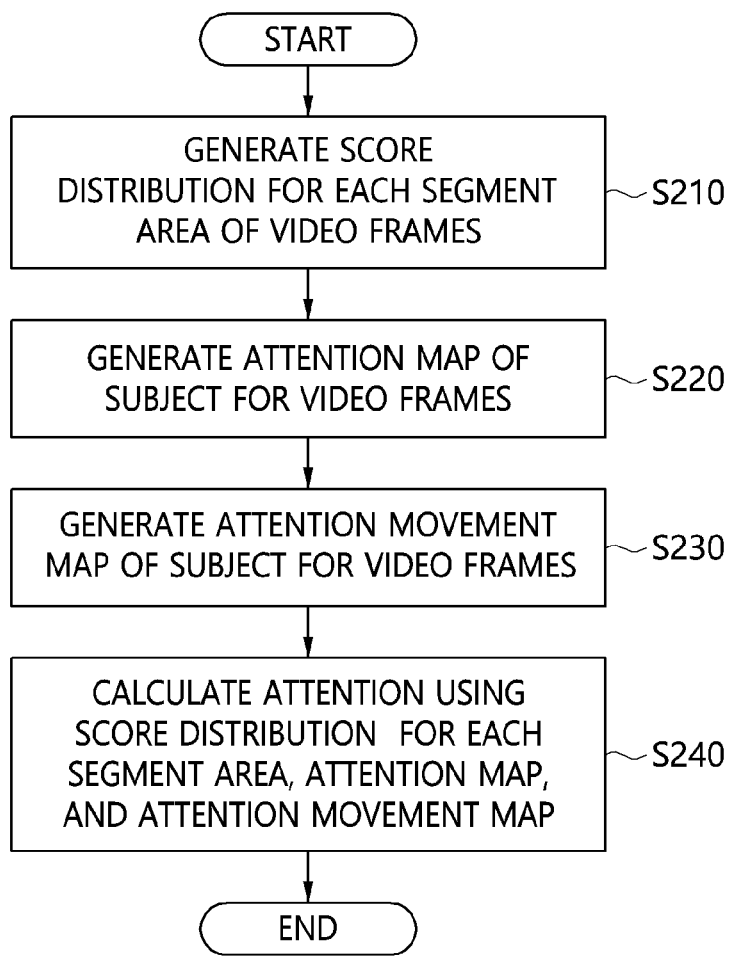
FIG. 2 is a flowchart illustrating a method for supporting an attention test based on an attention map and an attention movement map according to an embodiment of the present invention.

FIG. 2 is a flowchart illustrating a method for supporting an attention test based on an attention map and an attention movement map according to an embodiment of the present invention.

Referring to FIG. 2, in the method for supporting an attention test based on an attention map and an attention movement map, which is performed by the apparatus for supporting an attention test, a score distribution for each segment area is defined for frames satisfying preset conditions, among video frames, at step S210.

Hereinafter, generating a score distribution for each segment area at step S210 will be described in detail with reference to FIGS. 3 to 5.

Figure 3:
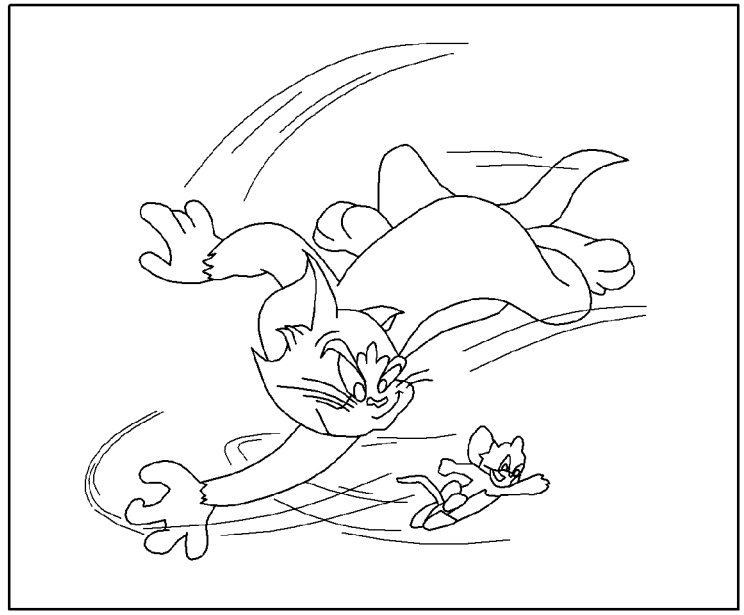
FIG. 3 is a view illustrating a specific frame of playing video according to an embodiment of the present invention.

FIG. 3 is a view illustrating a specific frame of playing video according to an embodiment of the present invention.

Here, the frame illustrated in FIG. 3, for which a score distribution for each area and an attention map are generated, may be a frame included in main scenes satisfying preset conditions, among the scenes of the video.

The frame illustrated in FIG. 3 is any one of the frames of a scene corresponding to the main scene of the video, and shows a cat chasing a mouse.

Here, the main scene or main video frame information may be selected using an automatic generation method based on scene change information, information about appearance and movement of an object of interest in a scene, key-frame information, sample survey and statistical analysis on a scene, deep learning, and the like, or using a method in which the main scene or main video frame information is specified by an expert, and consecutive scenes or frames in a certain section, rather than a single scene or frame, may be selected.

In the method for supporting an attention test according to an embodiment of the present invention, a score distribution for each gazed area may be set based on the frame illustrated in FIG. 3.

Figure 4:
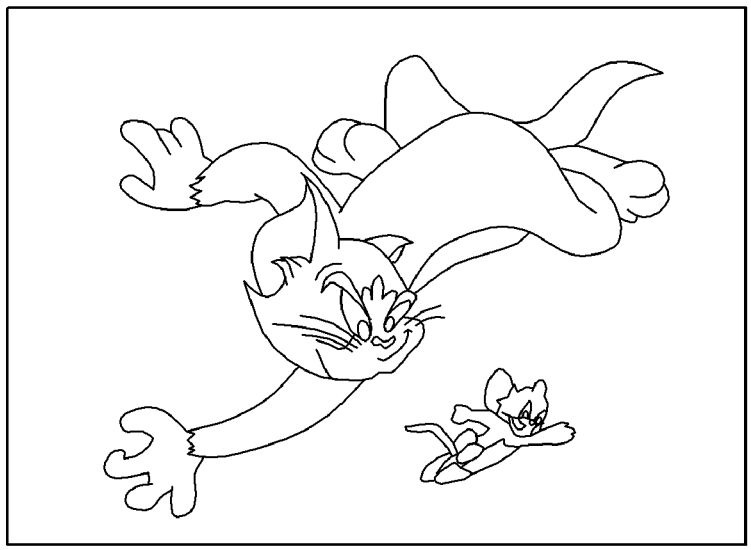
FIG. 4 is a view illustrating detection of an object of interest corresponding to the specific frame of FIG. 3.

FIG. 4 is a view illustrating detection of an object of interest corresponding to the specific frame of FIG. 3.

The object detection result illustrated in FIG. 4 may include only objects of interest due to exclusion of a background, a motion effect, and the like from the main scene frame of FIG. 3.

Referring to FIG. 4, it can be seen that a cat and a mouse are detected as objects of interest in the frame of FIG. 3.

Figure 5:
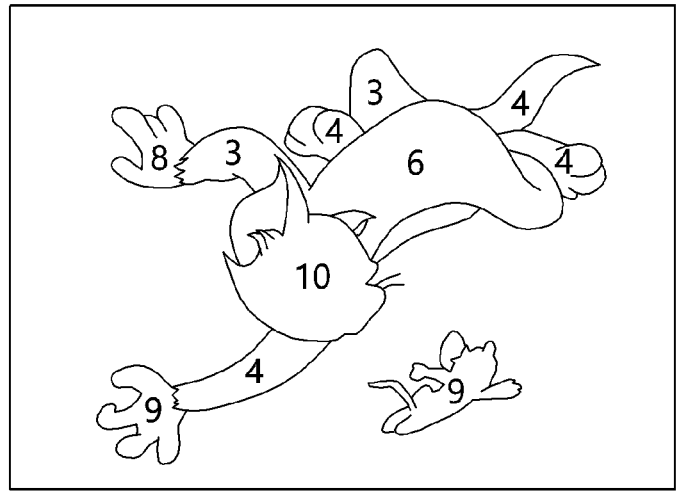
FIG. 5 is an exemplary view illustrating that the object of interest in FIG. 4 is segmented into component units and that a score distribution for each segment area is defined.

FIG. 5 is an exemplary view illustrating that the objects of interest in FIG. 4 are segmented into component units and that a score distribution for each segment area is defined.

Referring to FIG. 5, it can be seen that the cat, which is an object of interest having a relatively large size, is segmented into hands, arms, a face, a torso, legs, feet, and a tail. Also, it can be seen that the mouse, which is an object of interest having a relatively small size, is not segmented.

That is, only when an object of interest has a size greater than a preset size may the object of interest be segmented into component units.

Also, the object of interest may be segmented such that the sizes of the components are maintained equal to or greater than a preset size.

Here, a main scene object detection and segmentation unit may use an instance segmentation method to which recent deep learning is applied or a background removal and object segmentation method based on conventional image processing.

Also, after the cat is segmented into component units, such as a face, arms, and the like, scores are given to the respective component units, whereby a score distribution for each segment area is defined. For example, relatively high scores of 10 and 9 may be respectively given to the face and the left hand, with which the cat is trying to catch the mouse, and relatively low scores may be given to the tail, the legs, and the like.

When a score distribution for each segment area of the component units is defined as described above, various methods such as deep learning, sample survey and statistical analysis, detection of movement/change of an object in video, analysis of semantic information between objects, manual assignment by an expert and the like may be applied.

Subsequently, in the method for supporting an attention test according to an embodiment of the present invention, an attention map and an attention movement map of a subject are generated for the video frames through analysis of the gaze point of the subject at steps S220 and S230.

Hereinafter, generating an attention map and an attention movement map at steps S220 and S230 will be described in detail with reference to FIGS. 6 to 7.

Figure 6:
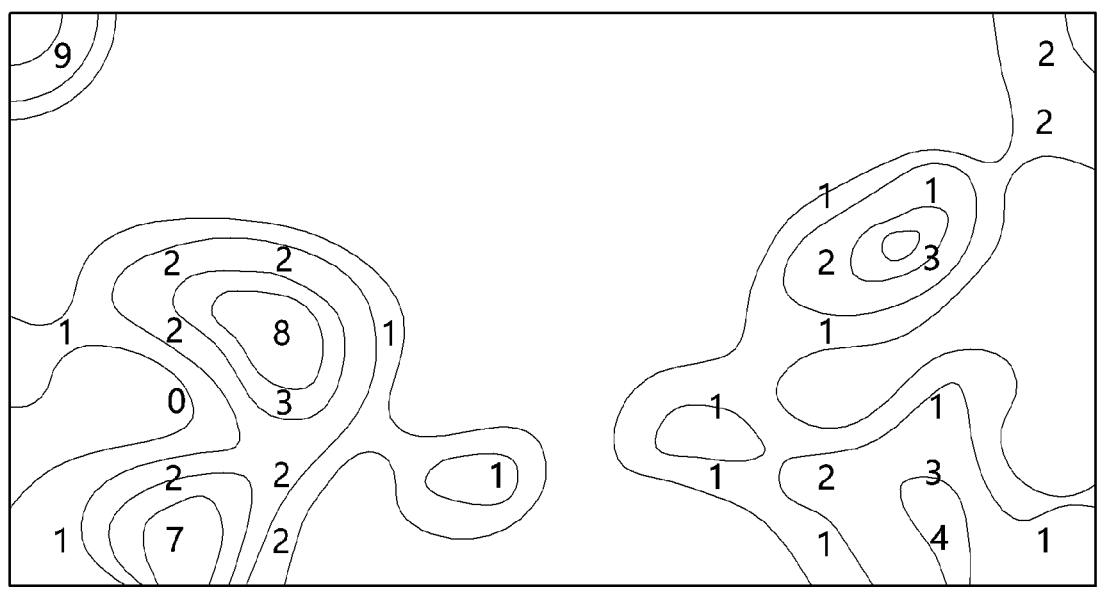
FIG. 6 is an exemplary view illustrating a subject's attention map generated based on a method for supporting an attention test according to an embodiment of the present invention.

FIG. 6 is an exemplary view illustrating a subject's attention map generated based on a method for supporting an attention test according to an embodiment of the present invention.

Here, the attention map of the subject may be generated by detecting the face area of the subject in the input image of the subject and estimating the coordinates of the gaze based on detection of pupils or directly detecting the coordinates of the gaze point on a screen.

Here, in order to correct or calculate the coordinates of the gaze point of the subject, the result of estimating the head pose of the subject may be used.

Consequently, the overall distribution of the location where the gaze of the subject remains in the segment area of the object of interest in the main scene or the main video frame of the video content may be managed using all of the frequency, distribution, and the like of the coordinates of the gaze point.

Figure 7:
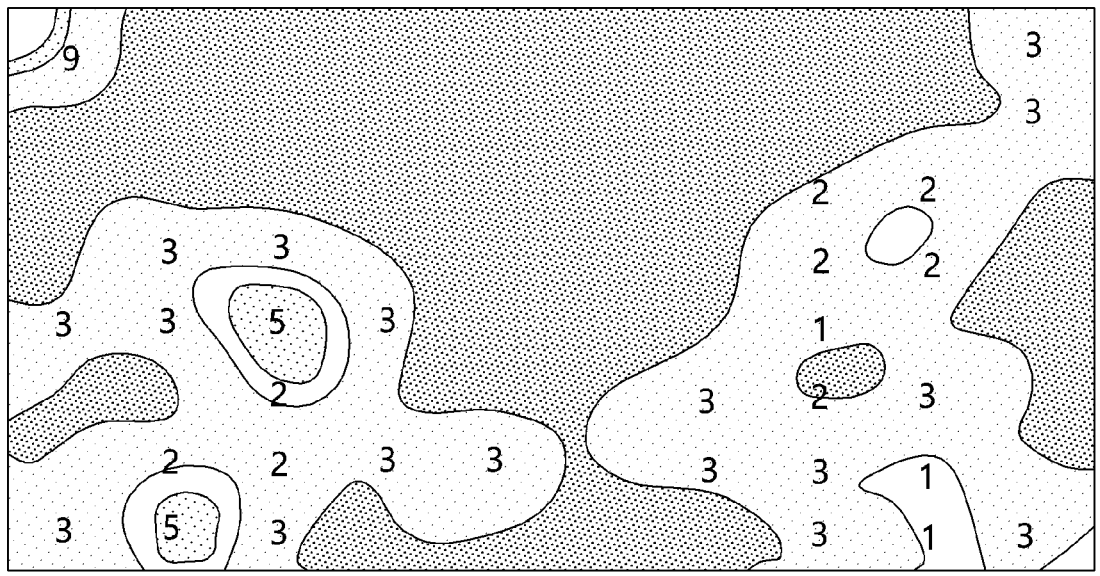
FIG. 7 is an exemplary view illustrating a subject's attention movement map generated based on a method for supporting an attention test according to an embodiment of the present invention.

FIG. 7 is an exemplary view illustrating a subject's attention movement map generated based on a method for supporting an attention test according to an embodiment of the present invention.

Like an attention map, an attention movement map of a subject may be generated by detecting the face area of the subject in the input image of the subject and estimating the coordinates of the gaze based on detection of pupils or directly detecting the coordinates of the gaze point on a screen.

Here, the attention movement map may include information about an attention movement vector, which indicates whether the gaze point of the subject stays in a specific area for a time equal to or greater than a preset time (fixation) or is quickly moving to another area (saccade).

Here, the preset time for determining the fixation may be defined depending on the characteristics of the video content or in consideration of movement of the object of interest in the video, the speed of change thereof, and the like.

Subsequently, in the method for supporting an attention test according to an embodiment of the present invention, the attention of the subject is analyzed using the score distribution for each segment area, the attention map, and the attention movement map at step S240.

Here, analyzing the attention of the subject at step S240 may be the process of calculating the attention score pattern of the subject using the score distribution for each segment area, the attention map, and the attention movement map.

Figure 8:
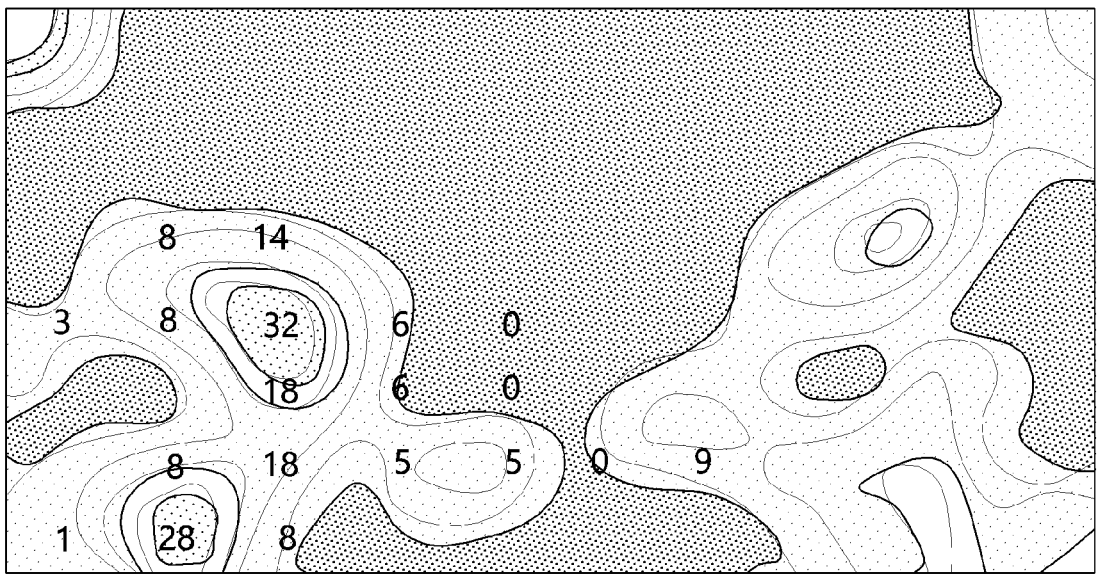
FIG. 8 is an exemplary view illustrating the process of analyzing the attention of a subject based on a method for supporting an attention test according to an embodiment of the present invention.

FIG. 8 is an exemplary view illustrating the process of analyzing the attention of a subject based on a method for supporting an attention test according to an embodiment of the present invention.

Referring to FIG. 8, it can be seen that an attention distribution map of a subject is generated based on a score distribution for each segment area, an attention map, and an attention movement map.

Here, the attention distribution map of the subject may be generated based on weight values of the score distribution for each segment area and on analysis of the correlation between the attention map and the attention movement map of the subject.

Alternatively, the attention distribution map of the subject may be generated based on the weight values of the score distribution for each segment area and on a result of operation performed on the 2D pattern values of the attention map and the attention movement map of the subject.

Here, calculating the attention of the subject at step S240 may include supporting screening or diagnosis of the subject in an automatic manner based on the attention map, the attention movement map, and a result of analysis of the correlation between the attention calculation result and the development test result of the subject.

Here, in order to support screening or diagnosis of the subject, deep learning, a classifier, or the like may be used.

Figure 9:
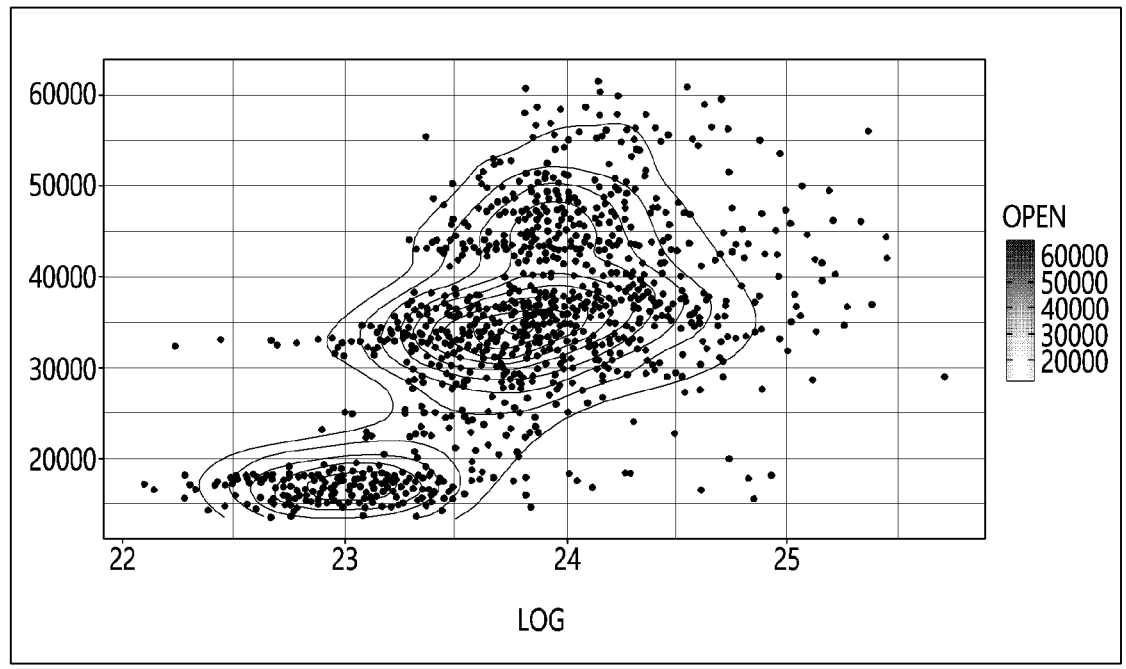
FIG. 9 is an exemplary view illustrating a result of analysis of the attention of a subject based on a method for supporting an attention test according to an embodiment of the present invention.

FIG. 9 is an exemplary view illustrating the result of analysis of the attention of a subject based on the method for supporting an attention test according to an embodiment of the present invention.

Figure 10:
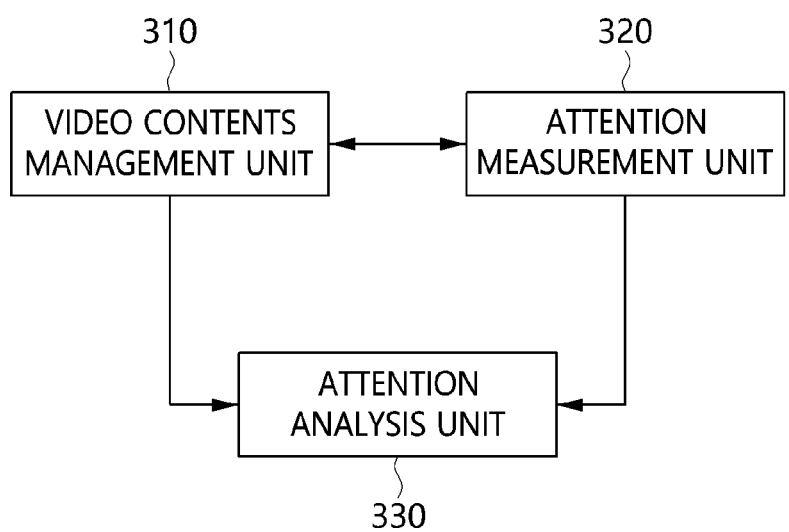
FIG. 10 is a block diagram illustrating an apparatus for supporting an attention test based on an attention map and an attention movement map according to an embodiment of the present invention.

FIG. 10 is a block diagram illustrating an apparatus for supporting an attention test based on an attention map and an attention movement map according to an embodiment of the present invention.

Referring to FIG. 10, the apparatus for supporting an attention test based on an attention map and an attention movement map according to an embodiment of the present invention includes a video contents management unit 310 for generating a score distribution for each segment area of frames satisfying preset conditions, among the frames of video, an attention measurement unit 320 for generating an attention map corresponding to the frames based on the distribution of the gaze point of a subject and generating an attention movement map corresponding to the frames based on information about movement of the gaze point of the subject, and an attention analysis unit 330 for calculating the attention of the subject using the score distribution for each segment area, the attention map, and the attention movement map.

Here, the video contents management unit 310 may detect an object of interest in the frames, segment the object of interest into component units, and define the score distribution for each segment area based on the result of segmentation of the object of interest into component units.

Here, the video contents management unit 310 may generate a score distribution for each segment area that represents frames in a preset time section of the video.

Here, the attention measurement unit 320 may generate an attention map and an attention movement map that represent the frames in the preset time section.

Here, the score distribution for each segment area, the attention map, and the attention movement map may be generated in the form of 2D patterns corresponding to the frame of the video.

Here, the attention analysis unit 330 may calculate the attention based on the result of operation performed on the values of the 2D patterns of the score distribution for each segment area, the attention map, and the attention movement map.

Here, the attention analysis unit 330 may support screening or diagnosis of the subject in an automatic manner based on the attention map, the attention movement map, and the result of analysis of the correlation between the attention calculation result and the development test result of the subject.

Here, the attention movement map may include information about whether the gaze point of the subject stays in a specific area for a time longer than a preset time and information about the movement of the gaze point.

Here, the preset time may be set based on movement of the object of interest and information about the speed thereof.

Here, the attention measurement unit 320 may detect a face area in the image of the subject, detect the coordinates of the gaze point of the subject, and correct the coordinates of the gaze point based on the head pose of the subject, thereby generating an attention map and an attention movement map.

Figure 11:
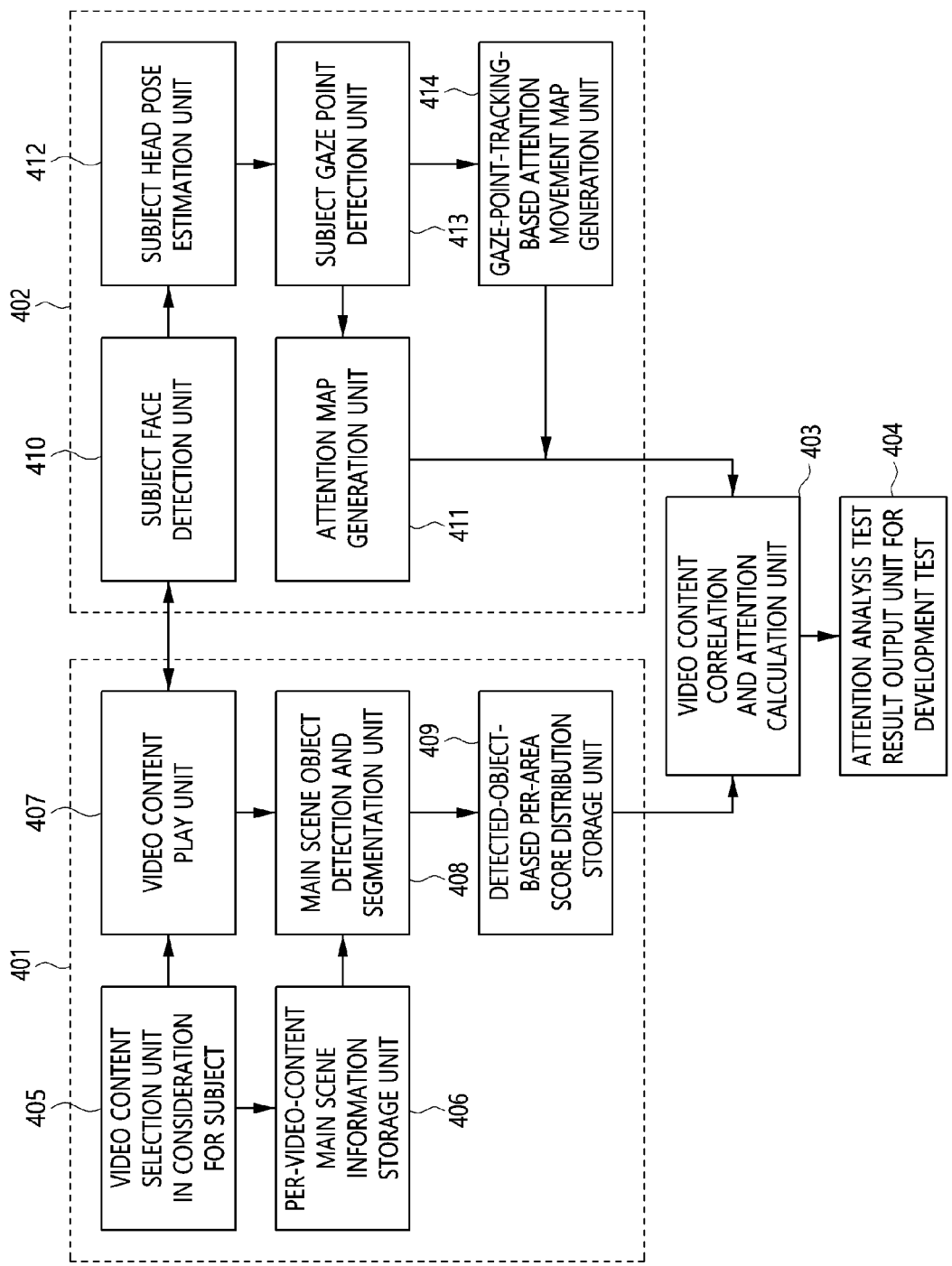
FIG. 11 is a block diagram illustrating in detail an apparatus for supporting an attention test based on an attention map and an attention movement map according to an embodiment of the present invention.

FIG. 11 is a block diagram illustrating in more detail the apparatus for supporting an attention test based on an attention map and an attention movement map according to an embodiment of the present invention.

Referring to FIG. 11, the apparatus for supporting an attention test based on an attention map and an attention movement map includes a video content management unit 401, an attention map and attention movement map generation unit 402 based on gaze-point tracking, a video content correlation and attention calculation unit 403, and an attention analysis test result output unit 404 for a development test.

Here, the video content management unit 401, the attention map and attention movement map generation unit 402, and the video content correlation and attention calculation unit 403 may be components respectively corresponding to the video contents management unit 310, the attention measurement unit 320, and the attention analysis unit 330 of FIG. 10.

The video content management unit 401 may include a video content selection unit 405, which is capable of selecting any of various types of previously produced video content in consideration of a subject so as to be suitable for the purpose of the test and personal characteristics of the subject by taking into consideration the age of the subject, the gender thereof, characteristics preferred thereby, and the test field therefor, and a video content play unit 407 for playing the selected video content on a screen.

Also, the video content management unit 401 includes a per-image-content main scene information storage unit 406 that contains information about a main scene or a main video frame based on which attention is capable of being analyzed in connection with previously produced video content, a main scene object detection and segmentation unit 408 for detecting an object of interest in the main scene or the main video frame and segmenting the detected object into component units, and a detected-object-based per-area score distribution storage unit 409 for generating, storing, and managing a distribution of weight values for respective segment areas of the detected object.

Here, the main scene or main video frame information may be selected using an automatic generation method based on scene change information, information about the appearance and movement of an object of interest in a scene, key-frame information, sample survey and statistical analysis on a scene, deep learning, and the like, or using a method in which the main scene or main video frame information is specified by an expert.

Here, the main scene and main video frame information may be selected from consecutive scenes or frames in a certain section, rather than a single scene or frame.

Also, the main scene object detection and segmentation unit 408 may use an instance segmentation method to which deep learning is applied or a background removal and object segmentation method based on conventional image processing.

Also, when a score distribution for each segment area of the detected object is generated, various methods such as sample survey and statistical analysis, detection of movement/change of the object in video, analysis of semantic information between objects, manual assignment by an expert, and the like may be applied thereto. Also a single score distribution for each segment area may be generated on a per-frame basis, or may be generated for a certain section of the video frame.

The attention map and attention movement map generation unit 402 based on gaze-point tracking may include a subject face detection unit 410 for detecting/tracking the face area of a subject in an input image in order to more accurately extract the gaze point of the subject, a subject head pose estimation unit 412 for correcting or calculating more accurate gaze point coordinates on a screen at which the subject is looking in a 3D space, and a subject gaze point detection unit 413 for estimating the coordinates of the gaze based on detection of pupils in a 3D space or directly detecting the coordinates of the gaze point on the screen.

Also, the attention map and attention movement map generation unit 402 based on gaze-point tracking includes an attention map generation unit 411 for generating an attention map having the characteristics of a heat-map based on the frequency and distribution of the coordinates of the gaze point of a subject, which are measured by the subject face detection unit 410, the subject head pose estimation unit 412, and the subject gaze point detection unit 413, and an attention movement map generation unit 414 for generating an attention movement map including information about an attention movement vector indicating whether the gaze point stays in a region of interest for a time equal to or longer than a certain time (fixation) or quickly moves to another region of interest (saccade).

Here, in order to detect the face of the subject, a conventional method, such as an algorithm using a conventional Viola-Jones AdaBoost classifier, or a deep-learning-based face detection algorithm may be used.

Here, tracking the head pose of a subject may use a genetic algorithm pose estimation method for estimating a 3D head pose using a conventional algorithm, a learning-based pose estimation method using various types of head pose data for various types of objects, an optimization-based pose estimation method for outputting a pose acquired by repeatedly minimizing the error between a 3D point and a projected 2D point using a gradient descent algorithm, a Levenberg-Marquardt algorithm, or the like, a geometric pose estimation method for estimating the 3D position and rotation of a 3D object based only on a single 2D image, or a deep-learning-based head pose estimation method.

Here, when the gaze point of a subject is detected using an infrared camera, a method of detecting the pupils of the subject and estimating the coordinates of the gaze in consideration of the distance from a display device in a 3D space or a method of detecting the coordinates of the gaze point based on deep learning may be used.

The attention map generation unit 411 may store and manage the overall distribution of the location where the gaze of the subject stays in the segment area of the object of interest in the main scene or main video frame of the video content using all of the frequency, the distribution, and the like of the coordinates of the gaze point.

The gaze-point-tracking-based attention movement map generation unit 414 may detect fixation or saccade by analyzing the relationship between the result of tracking the gaze point of the subject and time, and may generate a more accurate attention movement map by recognizing both fixation on the areas into which the object of interest is segmented and saccade with regard to whether the gaze is quickly moving in response to movement/change of the object in the scene.

Here, fixation may be defined as a value within a certain range depending on the characteristics of content, or the per-area score distribution storage unit 409 may contain a previously set value therefor for use according to the purpose of the test and the characteristics of video content by reflecting the movement/change speed of the object of interest in the image.

Here, generating the attention map and the attention movement map may comprise generating a single attention map and a single attention movement map for a single score distribution for each segment area of the detected object or generating a single attention map and a single attention movement map for consecutive main scenes in a certain section or for each section of the main video frame.

Meanwhile, an existing or commercial eye tracker may be used in place of the subject face detection unit 410, the subject head pose estimation unit 412, and the subject gaze point detection unit 413 for generating an attention map and an attention movement map.

When the attention map and the attention movement map are generated, the video content correlation and attention calculation unit 403 calculates a score for the attention of the subject for each segment area in the detected object and for the main scene, the main video frame, or a certain section using information previously stored in the per-area score distribution storage unit 409 based on the detected object in the main scene of the video content, thereby calculating various types of statistical data.

Also, the attention analysis test result output unit 404 for a development test may support the development test based on various methods, such as the correlation between the distribution of attention and a development test result, and the like using statistical information of attention-related factors, such as the correlation between content and attention in which the characteristics of the content are taken into consideration, an object of interest using the attention map and the attention movement map, the characteristics of the distribution of attention, and an attention movement vector.

Figure 12:
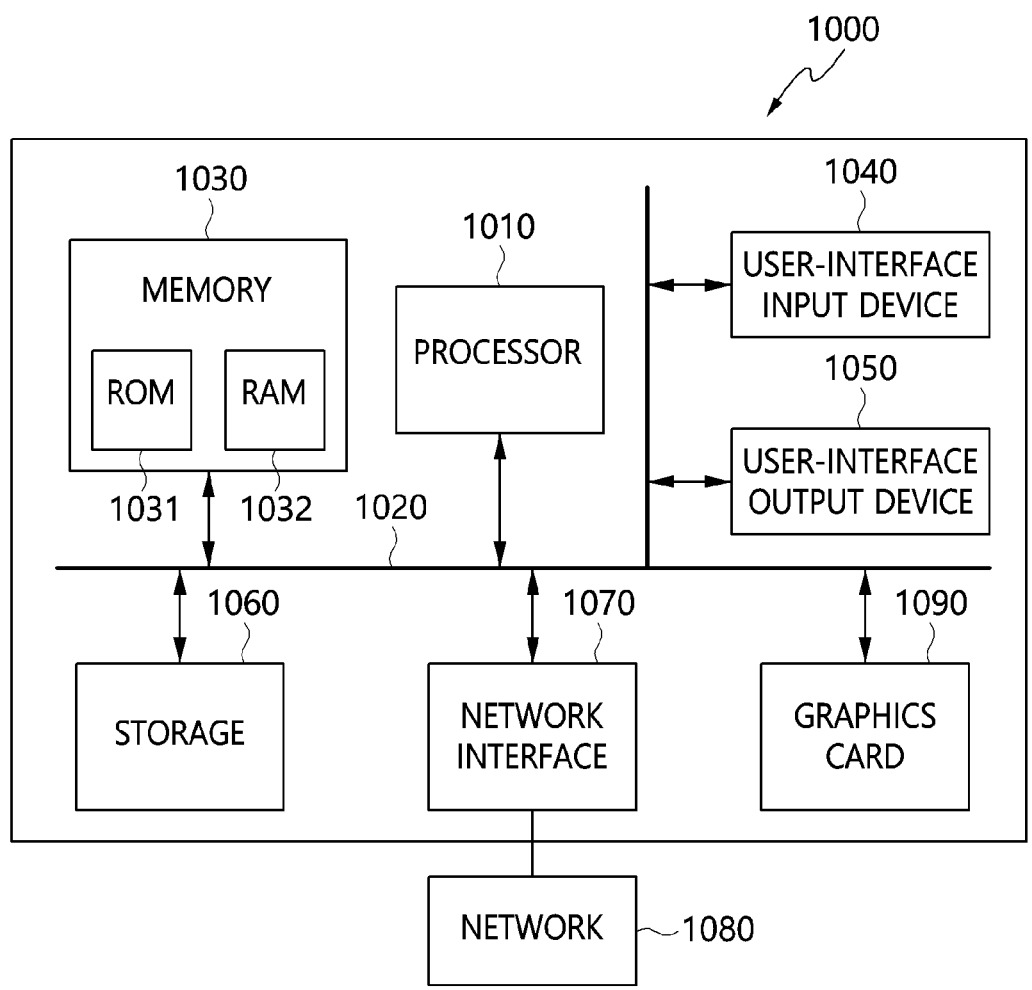
FIG. 12 is a view illustrating a computer system configuration according to an embodiment.

FIG. 12 is a view illustrating a computer system configuration according to an embodiment.

The apparatus for supporting an attention test based on an attention map and an attention movement map according to an embodiment may be implemented in a computer system 1000 including a computer-readable recording medium.

The computer system 1000 may include one or more processors 1010, memory 1030, a user-interface input device 1040, a user-interface output device 1050, storage 1060, and a graphics card 1090, which communicate with each other via a bus 1020. Also, the computer system 1000 may further include a network interface 1070 connected to a network 1080. The processor 1010 may be a central processing unit or a semiconductor device for executing a program or processing instructions stored in the memory 1030 or the storage 1060. The memory 1030 and the storage 1060 may be storage media including at least one of a volatile medium, a nonvolatile medium, a detachable medium, a non-detachable medium, a communication medium, and an information delivery medium. For example, the memory 1030 may include ROM 1031 or RAM 1032.

According to the present invention, an object of interest in video frames is segmented into component units, and a score distribution is generated for each segment area, whereby the attention of a subject may be automatically calculated.

Also, according to the present invention, the attention of a subject is measured using all of the frequency of the gaze point of the subject, the distribution thereof, and information about movement thereof, whereby the attention of the subject may be accurately and objectively measured.

Specific implementations described in the present invention are embodiments and are not intended to limit the scope of the present invention. For conciseness of the specification, descriptions of conventional electronic components, control systems, software, and other functional aspects thereof may be omitted. Also, lines connecting components or connecting members illustrated in the drawings show functional connections and/or physical or circuit connections, and may be represented as various functional connections, physical connections, or circuit connections that are capable of replacing or being added to an actual device. Also, unless specific terms, such as "essential", "important", or the like, are used, the corresponding components may not be absolutely necessary.

Accordingly, the spirit of the present invention should not be construed as being limited to the above-described embodiments, and the entire scope of the appended claims and their equivalents should be understood as defining the scope and spirit of the present invention.

What is claimed is:

1. A method for supporting an attention test based on an attention map and an attention movement map, comprising:
    defining a score distribution for each segment area of frames satisfying preset conditions, among frames of video;
    generating an attention map corresponding to the frames based on a distribution of a gaze point of a subject;
    generating an attention movement map corresponding to the frames based on information about movement of the gaze point of the subject; and
    calculating an attention of the subject using the score distribution for each segment area, the attention map, and the attention movement map,
    wherein the attention movement map includes information about an attention movement vector, which indicates whether the gaze point of the subject stays in a specific area for a time equal to or greater than a preset time or is moving to another area based on the speed, and
    wherein the attention of the subject is generated based on weight values of the score distribution for each segment area and on analysis of the correlation between the attention map and the attention movement map of the subject.

2. The method of claim 1, wherein defining the score distribution for each segment area includes:
    detecting an object of interest in the frames;
    segmenting the object of interest into component units; and
    defining the score distribution for each segment area based on a result of segmentation of the object of interest into the component units.

3. The method of claim 2, wherein:
    defining the score distribution for each segment area comprises generating a score distribution for each segment area that represents frames in a preset time section in the video, and
    generating the attention map and generating the attention movement map comprise generating the attention map and the attention movement map that represent the frames in the preset time section.

4. The method of claim 3, wherein the score distribution for each segment area, the attention map, and the attention movement map correspond to 2-dimensional pattern forms corresponding to a frame of the video.

5. The method of claim 4, wherein calculating the attention of the subject comprises calculating the attention based on a result of operation performed on values of the 2-dimensional pattern forms of the score distribution for each segment area, the attention map, and the attention movement map.

6. The method of claim 5, wherein calculating the attention of the subject includes supporting screening or diagnosis of the subject in an automatic manner based on the attention map, the attention movement map, and a result of analysis of a correlation between a result of calculating the attention and a development test result.

7. The method of claim 5, wherein the attention movement map includes information about whether the gaze point of the subject stays in a specific area for a time longer than a preset time and the information about the movement of the gaze point.

8. The method of claim 7, wherein the preset time is set based on movement information and speed information of the object of interest.

9. The method of claim 5, wherein generating the attention map includes:
    detecting a face area in an image of the subject;
    detecting coordinates of the gaze point of the subject; and
    correcting the coordinates of the gaze point based on a head pose of the subject.

10. The method of claim 1, wherein the video corresponds to various video content produced in advance so as to be suitable for a test field and a purpose of a test.

11. An apparatus for supporting an attention test based on an attention map and an attention movement map, comprising:
    a video contents management unit for defining a score distribution for each segment area of frames satisfying preset conditions, among frames of video;
    an attention measurement unit for generating an attention map corresponding to the frames based on a distribution of a gaze point of a subject and generating an attention movement map corresponding to the frames based on information about movement of the gaze point of the subject; and
    an attention analysis unit for calculating an attention of the subject using the score distribution for each segment area, the attention map, and the attention movement map,
    wherein the attention movement map includes information about an attention movement vector, which indicates whether the gaze point of the subject stays in a specific area for a time equal to or greater than a preset time or is moving to another area based on the speed, and
    wherein the attention of the subject is generated based on weight values of the score distribution for each segment area and on analysis of the correlation between the attention map and the attention movement map of the subject.

12. The apparatus of claim 11, wherein the video contents management unit detects an object of interest in the frames, segments the object of interest into component units, and defines the score distribution for each segment area based on a result of segmentation of the object of interest into the component units.

13. The apparatus of claim 12, wherein:
    the video contents management unit defines a score distribution for each segment area that represents frames in a preset time section in the video, and
    the attention measurement unit generates the attention map and the attention movement map that represent the frames in the preset time section.

14. The apparatus of claim 13, wherein the score distribution for each segment area, the attention map, and the attention movement map correspond to 2-dimensional pattern forms corresponding to a frame of the video.

15. The apparatus of claim 14, wherein the attention analysis unit calculates the attention based on a result of operation performed on values of the 2-dimensional pattern forms of the score distribution for each segment area, the attention map, and the attention movement map.

16. The apparatus of claim 15, wherein the attention analysis unit supports screening or diagnosis of the subject in an automatic manner based on the attention map, the attention movement map, and a result of analysis of a correlation between a result of calculating the attention and a development test result.

17. The apparatus of claim 15, wherein the attention movement map includes information about whether the gaze point of the subject stays in a specific area for a time longer than a preset time and the information about the movement of the gaze point.

18. The apparatus of claim 17, wherein the preset time is set based on movement information and speed information of the object of interest.

19. The apparatus of claim 15, wherein the attention measurement unit detects a face area in an image of the subject, detects coordinates of the gaze point of the subject, and corrects the coordinates of the gaze point based on a head pose of the subject, thereby generating the attention map and the attention movement map.

20. The apparatus of claim 11, wherein the video corresponds to various video content produced in advance so as to be suitable for a test field and a purpose of a test.

* * * * *